(12) United States Patent
Bultman et al.

(10) Patent No.: US 9,908,882 B2
(45) Date of Patent: Mar. 6, 2018

(54) PROCESS FOR PREPARING HALOGENATED AZAINDOLE COMPOUNDS USING BOROXINE

(71) Applicant: ViiV HEALTHCARE UK (NO.4) LIMITED, Brentford, Middlesex (GB)

(72) Inventors: Michael S. Bultman, New Brunswick, NJ (US); Benjamin Cohen, New Brunswick, NJ (US); Francisco Gonzalez-Bobes, New Brunswick, NJ (US); Matthew R. Hickey, New Brunswick, NJ (US)

(73) Assignee: ViiV HEALTHCARE UK (NO.4) LIMITED, Brentford, Middlesex (GB)

( * ) Notice: Subject to any disclaimer, the term of this patent is extended or adjusted under 35 U.S.C. 154(b) by 0 days.

(21) Appl. No.: 15/529,537

(22) PCT Filed: Dec. 17, 2015

(86) PCT No.: PCT/US2015/066311
§ 371 (c)(1),
(2) Date: May 25, 2017

(87) PCT Pub. No.: WO2016/100633
PCT Pub. Date: Jun. 23, 2016

(65) Prior Publication Data
US 2017/0298064 A1    Oct. 19, 2017

Related U.S. Application Data

(60) Provisional application No. 62/093,645, filed on Dec. 18, 2014.

(51) Int. Cl.
| | |
|---|---|
| *C07D 401/00* | (2006.01) |
| *C07D 471/04* | (2006.01) |
| *C07D 401/14* | (2006.01) |
| *C07D 249/08* | (2006.01) |
| *C07F 9/6561* | (2006.01) |
| *C07F 5/02* | (2006.01) |
| *C07C 17/02* | (2006.01) |

(52) U.S. Cl.
CPC ........... *C07D 471/04* (2013.01); *C07C 17/02* (2013.01); *C07D 249/08* (2013.01); *C07D 401/14* (2013.01); *C07F 5/022* (2013.01); *C07F 9/6561* (2013.01)

(58) Field of Classification Search
CPC .................................................... C07D 471/04
USPC ........................................................ 546/201
See application file for complete search history.

(56) References Cited

U.S. PATENT DOCUMENTS 8,889,869 B2 * 11/2014 Eastgate ............... C07F 9/6561
                                                                           546/113

FOREIGN PATENT DOCUMENTS

| WO | WO 2007/127731 A1 | 11/2007 |
| WO | WO 2009/158394 A1 | 12/2009 |
| WO | WO 2013/119625 A1 | 8/2013 |

OTHER PUBLICATIONS

Chen et al. J. Org. Chem. 2014, 79, 8757-8767.*
Chen, J. Org. Chem. 2014, 79, 8757-8767.*
Wengryniuk, Org. Lett., vol. 15, No. 4, 792-795 2013.*
Chen, et al. "Synthesis of the 6-Azaindole Containing HIV-1 Attachment Inhibitor Pro-Drug, BMS-663068". The Journal of Organic Chemistry, 79(18):8757-8767 (Sep. 19, 2014).
Wengryniuk, et al. "Regioselective Bromination of Fusd Heterocyclic N-Oxides". Organic Letters, 15(4):792-795 (Feb. 15, 2013).

* cited by examiner

*Primary Examiner* — Nizal Chandrakumar
(74) *Attorney, Agent, or Firm* — Robert H. Brink; Edward R. Gimmi; William R. Majarian

(57) ABSTRACT

A process for preparing halogenated azaindole compounds makes use of stable reagents including a brominating reagent, a boroxine and a sulfonic anhydride to enhance the selectivity and yield of the final product. In addition, the process is associated with various other advantages, including the ability to recycle reagents, cost reduction, and improved manufacturability.

2 Claims, No Drawings

PROCESS FOR PREPARING HALOGENATED AZAINDOLE COMPOUNDS USING BOROXINE

CROSS REFERENCE TO RELATED APPLICATION

This application is a § 371 of International Application No. PCT/US2015/066311, filed 17 Dec. 2015, which claims the benefit of U.S. Provisional Application No. 62/093,645, filed 18 Dec. 2014, which are incorporated herein in their entireties.

FIELD OF THE INVENTION

The present invention relates to a process for preparing halogenated azaindole compounds which are used in obtaining HIV attachment inhibitor compounds useful as antivirals. In particular, the invention provides methods of making the piperazine prodrug compound identified as 1-benzoyl-4-[2-[4-methoxy-7-(3-methyl-1H-1,2,4-triazol-1-yl)-1-[(phosphonooxy)methyl]-1H-pyrrolo[2,3-c]pyridin-3-yl]-1,2-dioxoethyl]-piperazine, as well as certain intermediates thereof. The invention also relates to the compounds produced by the processes herein.

BACKGROUND OF THE INVENTION

HIV-1 (human immunodeficiency virus-1) infection remains a major medical problem, with tens of millions of people still infected worldwide at the end of 2011. The number of cases of HIV and AIDS (Acquired Immuno Deficiency Syndrome) has risen rapidly. In 2005, for example, approximately 5 million new infections were reported and 3.1 million people died from AIDS. Despite continued advances in HIV treatment options, the development of new antiretroviral drugs and regimens continues to represent an important area of unmet medical need due to long-term tolerability concerns and the emergence of viral strains resistant to current therapies. To date, the approved therapies to treat HIV infection fall into 4 general classes: (1) reverse-transcriptase inhibitors, (2) protease inhibitors, (3) integrase inhibitors and (4) entry inhibitors. Examples of available drugs for the treatment of HIV include nucleoside reverse transcriptase (RT) inhibitors or approved single pill combinations: zidovudine (or AZT or RETROVIR®), didanosine (or VIDEX®), stavudine (or ZERIT®), lamivudine (or 3TC or EPIVIR®), zalcitabine (or DDC or HIVID®), abacavir succinate (or ZIAGEN®), Tenofovir disoproxil fumarate salt (or VIREAD®), emtricitabine (or FTC or EMTRIVA®), COMBIVIR® (contains -3TC plus AZT), TRIZIVIR® (contains abacavir, lamivudine, and zidovudine), EPZICOM® (contains abacavir and lamivudine), TRUVADA® (contains VIREAD® and EMTRIVA®); non-nucleoside reverse transcriptase inhibitors: nevirapine (or VIRAMUNE®), delavirdine (or RESCRIPTOR®) and efavirenz (or SUSTIVA®), ATRIPLA® (TRUVADA®+SUSTIVA®), and etravirine, and peptidomimetic protease inhibitors or approved formulations: saquinavir, indinavir, ritonavir, nelfinavir, amprenavir, lopinavir, KALETRA®(lopinavir and Ritonavir), darunavir, atazanavir (REYATAV), and tipranavir (APTIVUS®), and integrase inhibitors such as raltegravir (ISENTRESS®), and entry inhibitors such as enfuvirtide (T-20) (FUZEON®) and maraviroc (SELZENTRY®).

The identification of potent, orally active antiretrovirals with a unique mechanism of action led to HIV attachment inhibitors a novel subclass of antiviral compounds that bind to the HIV surface glycoprotein gp120, and interfere with the interaction between the surface protein gp120 and the host cell receptor CD4. Thus, they prevent HIV from attaching to the human CD4 T-cell, and block HIV replication in the first stage of the HIV life cycle. The properties of HIV attachment inhibitors have been improved in an effort to obtain compounds with maximized utility and efficacy as antiviral agents.

One HIV attachment inhibitor compound, in particular, has now shown considerable prowess against HIV. This compound is identified as 1-(4-benzoyl-piperazin-1-yl)-2-[4-methoxy-7-(3-methyl-[1,2,4]triazol-1-yl)-1H-pyrralo [2,3-c]pyridine-3-yl]-ethane-1,2-dione, and is set forth and described in U.S. Pat. No. 7,354,924, which is incorporated herein in its entirety: The compound is represented by the formula below:

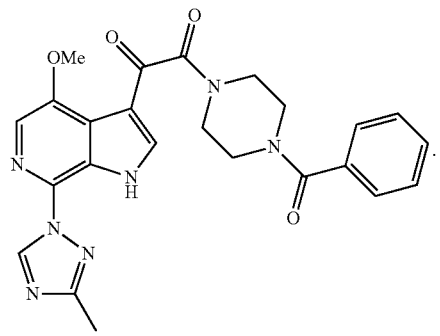 [SMILES: COc1cnc(-n2cnc(C)n2)c2[nH]cc(C(=O)C(=O)N3CCN(C(=O)c4ccccc4)CC3)c12]

The above compound is the parent compound of the prodrug known as 1-benzoyl-4-[2-[4-methoxy-7-(3-methyl-1H-1,2,4-triazol-1-yl)-1-[(phosphonooxy)methyl]-1H-pyrrolo[2,3-c]pyridin-3-yl]-1,2-dioxoethyl]-piperazine. It is set forth and described in U.S. Pat. No. 7,745,625, which is incorporated by reference herein it its entirety. The compound is represented by the formula below:

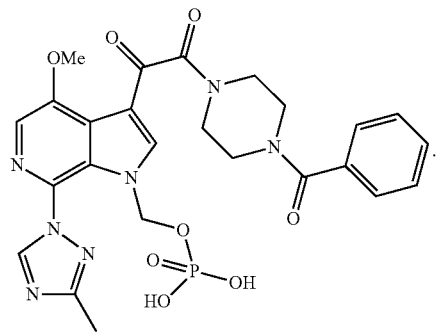 [SMILES: COc1cnc(-n2cnc(C)n2)c2c1c(C(=O)C(=O)N1CCN(C(=O)c3ccccc3)CC1)cn2COP(=O)(O)O]

Various methods for making this prodrug compound have been set forth, including those detailed in the '625 reference. In particular, the '625 reference includes various methods for acylation, alkylation and phosphorylation. Another patent reference, U.S. Pat. No. 8,436,168 entitled "Methods of Making HIV Attachment Inhibitor Prodrug Compound and Intermediates", also details various procedures for making the piperazine prodrug compound. These include a multi-step process which uses the compound

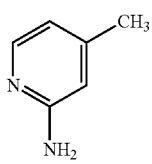

as a starting material, which is subsequently brominated, and then nitrated. Further on, a triazolyl moiety is added to the compound before further attaching the piperazine moiety separated by dual carbonyl groups. Yet another patent reference, U.S. Pat. No. 8,889,869 filed Feb. 6, 2013, entitled "Methods for the Preparation of HIV Attachment Inhibitor Piperazine Prodrug Compound", also details procedures for making the compound. These include a multi-step process which uses the compound N-sulfonylated pyrrole as a starting material, which is subsequently subjected to a Friedel-Crafts acylation reaction, Pictet-Spengler cyclization, two oxidation reactions followed by bromination, deprotection and a second Friedel-Crafts acylation. Further on, the piperazine moiety is incorporated by amidation of the dual carbonyl groups followed by the copper catalyzed reaction to install the triazolyl moiety.

What is now needed in the art are new methods of making the halogenated azaindole compounds so as to prepare piperazine prodrug compounds which are useful against HIV. The methods should be economical and also be able to produce the halogenated azaindole in high yield and selectivity.

SUMMARY OF THE INVENTION

In a first embodiment, the invention provides a process for preparing a compound of formula I,

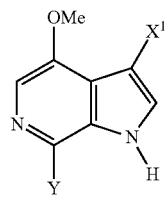
(I)

said process comprising the steps of:
(a) performing an oxidation reaction on the compound

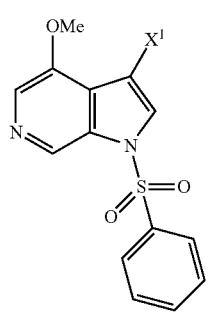

to yield the compound

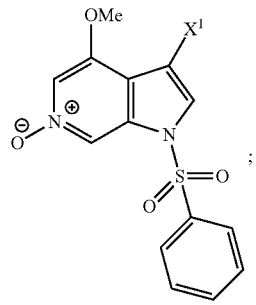

(b) performing a bromination reaction in the presence of one or more boroxine compounds on the compound obtained in step (a) to obtain the compound

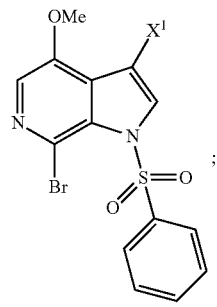

and
(c) performing a deprotection reaction on the compound obtained in step (b) to prepare the compound of formula I above;
wherein $X^1$ is selected from the group of H,

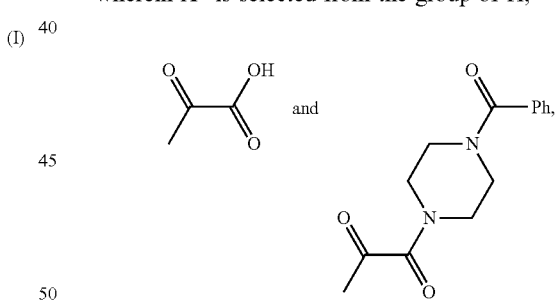

and Y is Br.

In another embodiment, the present invention provides a process for preparing a compound of formula II (II)
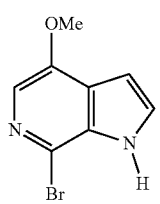

said process comprising the steps of:
(a) performing an oxidation reaction on the compound

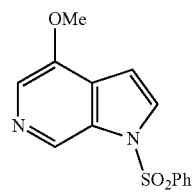

using H₂O₂, phthalic anhydride, and solvent to yield the compound

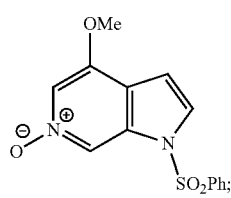

and
(b) performing a bromination reaction on the compound obtained in step (a) using one or more boroxine compounds along with a bromide source and an activating agent to obtain the compound

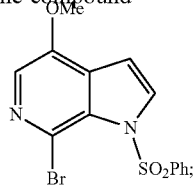

and
(c) performing a deprotection reaction on the compound obtained in step (b) using either substantially pure toluene or toluene in combination with a solvent, followed by crystallization, to prepare the compound of formula II or its salts thereof.

In a further embodiment, the present invention provides a method of making a compound of formula III

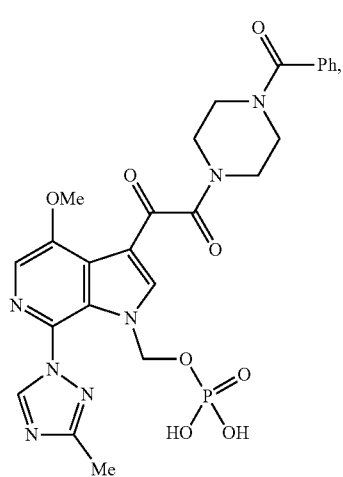

(III)

said process comprising the steps of:
(a) performing an oxidation reaction on the compound

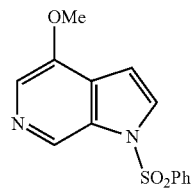

using H₂O₂, phthalic anhydride and dichloromethane to yield the compound

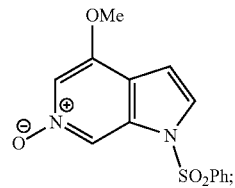

and
(b) performing a bromination reaction on the compound obtained in step (a) using one or more boroxine compounds along with a bromide source and an activating agent to obtain the compound

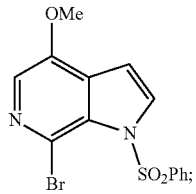

(c) performing a deprotection reaction on the compound obtained in step (b) using either substantially pure toluene or toluene in combination with a solvent, followed by crystallization, to obtain the compound

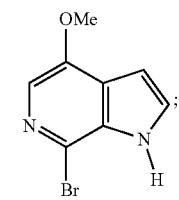 [SMILES: COc1cnc(Br)c2[nH]ccc12]

(d) reacting the compound obtained in step (c) to obtain the compound

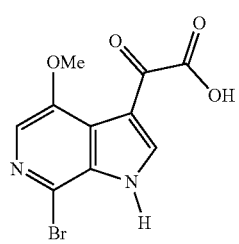 [SMILES: COc1cnc(Br)c2[nH]cc(C(=O)C(=O)O)c12]

followed by an activation reaction and coupling with the compound

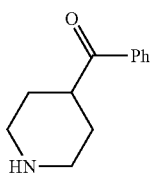

to produce the compound

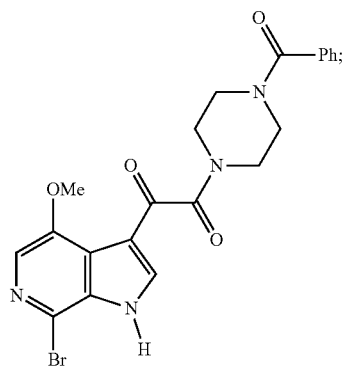 [SMILES: COc1cnc(Br)c2[nH]cc(C(=O)C(=O)N3CCN(C(=O)c4ccccc4)CC3)c12]

and
(e) adding the triazolyl compound

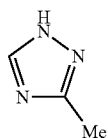

in the presence of Cu ion and a ligand to obtain the compound

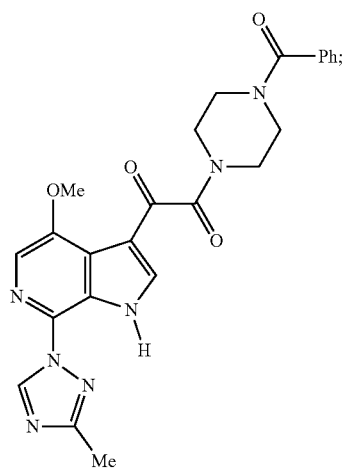 [SMILES: COc1cnc(-n2cnc(C)n2)c2[nH]cc(C(=O)C(=O)N3CCN(C(=O)c4ccccc4)CC3)c12]

wherein said ligand is selected from the group of 1,2-diaminocyclohexane, trans-1,2-diaminocyclohexane, cis-/trans-diaminocyclohexane, cis-N,N'-dimethyl-1,2-diaminocyclohexane, trans-N,N-dimethyl-1,2-di- aminocyclohexane, cis-/trans-N,N'-dimethyl-1,2-diaminocyclohexane, 1,2-diaminoethane, N,N'-dimethyl-1,2-diaminoethane, 1,10-phenanthroline, 4,7-diphenyl-1,10-phenantroline, 5-methyl-1,10-phenanthroline, 5-chloro-1,10-phenantroline, and 5-nitro-1,10-phenanthroline; and
(f) reacting the compound obtained in step (e) with (t-BuO)$_2$POOCH$_2$Cl to produce the compound

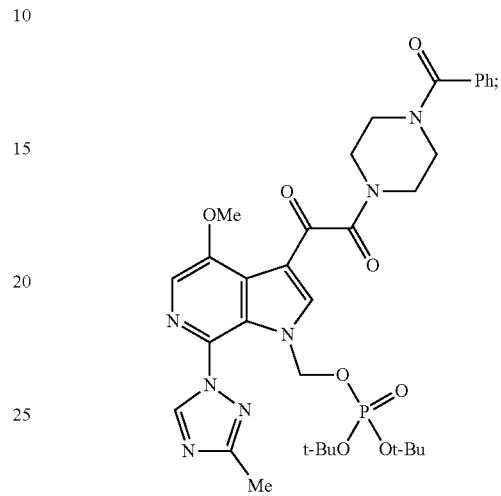

and reacting
(g) the compound obtained in step (f) with an acid, such as acetic acid, to yield the compound of formula III above.

The invention in further embodiments is also directed to each of the compounds of formulas I, II and III herein which are produced by the processes herein set forth.

The present invention is directed to these, as well as other important ends, hereinafter described.

DETAILED DESCRIPTION OF THE EMBODIMENTS

It will be understood that any given exemplary embodiment can be combined with one or more additional exemplary embodiments. As used herein, the singular forms "a", "an", and "the" include plural reference unless the context clearly dictates otherwise.

Unless otherwise specifically set forth, many reagents have been identified herein by their commonly accepted letter abbreviations in the art for ease of reference.

In addition, unless otherwise specifically set forth elsewhere in the application, the following terms may be used herein, and shall have the following meanings:

An "alkyl" group refers to a saturated aliphatic hydrocarbon including straight chain and branched chain groups. Preferably, the alkyl group has 1 to 20 carbon atoms (whenever a numerical range; e.g., "1-20", is stated herein, it means that the group, in this case the alkyl group may contain 1 carbon atom, 2 carbon atoms, 3 carbon atoms, etc. up to and including 20 carbon atoms). More preferably, it is a medium size alkyl having 1 to 10 carbon atoms. Most preferably, it is a lower alkyl having 1 to 4 carbon atoms. The alkyl group may be substituted or unsubstituted.

The term "$C_{1-6}$ alkyl" as used herein and in the claims means straight or branched chain alkyl groups with up to and including 6 carbon atoms, such as methyl, ethyl, propyl, isopropyl, butyl, isobutyl, t-butyl, amyl, hexyl and the like.

An "aryl" "Aryl" or "Ar" group refers to an all carbon monocyclic or fused-ring polycyclic (i.e., rings which share adjacent pairs of carbon atoms) groups having a completely conjugated pi-electron system. Examples, without limitation, of aryl groups are phenyl, napthalenyl and anthracenyl. The aryl group may be substituted or unsubstituted.

The abbreviations used in the present application are well-known to those skilled in the art. Some of the abbreviations used are as follows:

$Ac_2O$: acetic anhydride

Boroxines: General term to refer to cyclic trimeric boronic acid anhydrides; these will include the trialkylboroxines such as trimethylboroxine, and also the triarylboroxines such as triphenylboroxine t-Bu: tert-butyl $K_3PO_4$: potassium phosphate tribasic DCM: dichlormethance HCl: Hydrochloric acid $H_2O_2$: Hydrogen peroxide IPA: isopropyl alcohol mCPBA: m-Chloroperbenzoic acid $Ms_2O$: methanosulfonic anhydride NaOH: sodium hydroxide $Oct_4NBr$: Tetraoctylammonium bromide Tris: 2-amino-2-(hydroxymethyl)propane-1,3-diol In a first aspect, the present invention provides a process for preparing a compound of formula I,

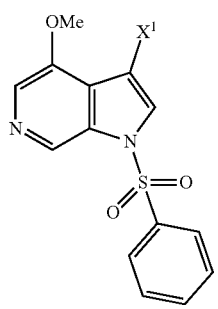

(I)

said process comprising the steps of:

(a) performing an oxidation reaction on the compound

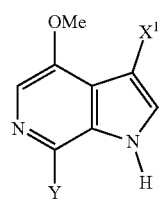

to yield the compound

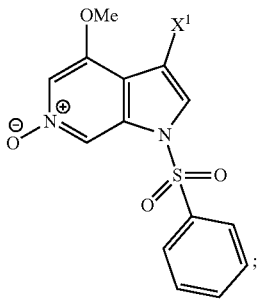

(b) performing a bromination reaction in the presence of one or more boroxine compounds on the compound obtained in step (a) to obtain the compound

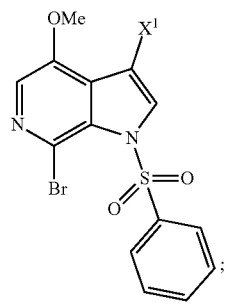

and (c) performing a deprotection reaction on the compound obtained in step (b) to obtain the compound of formula I above;

wherein $X^1$ is selected from the group of H,

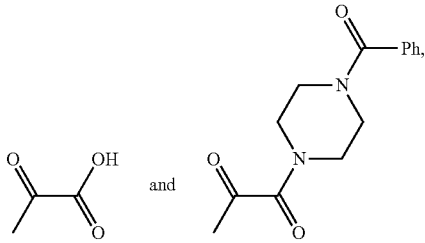

and Y is Br.

In a first embodiment of the first aspect, the oxidation reaction is carried out using oxidizing agents selected from the group of catalytic methyltrioxorhenium (MTO) and hydrogen peroxide urea complex (UHP), m-CPBA (m-chloroperoxybenzoic acid), a mixture of $Ac_2O$ and $H_2O_2$, and a mixture of phthalic anhydride and $H_2O_2$.

In a second embodiment of the first aspect, the compound

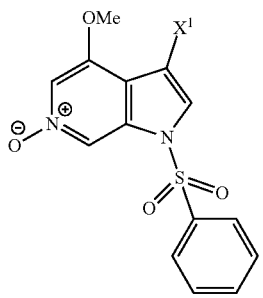

obtained in step (a) is treated with aqueous Na$_2$SO$_3$ followed by the addition of aqueous K$_3$PO$_4$.

In a third embodiment of the first aspect, the compound

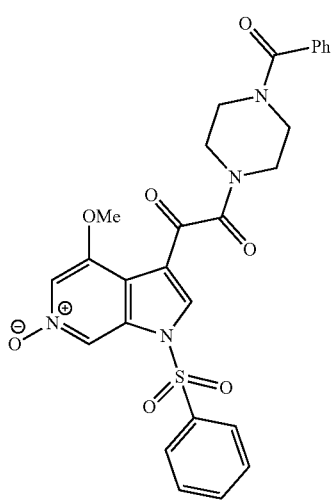 [SMILES: COc1c[n+]([O-])cc2c1c(C(=O)C(=O)N1CCN(C(=O)c3ccccc3)CC1)cn2S(=O)(=O)c1ccccc1]

obtained in step (a) is a crystalline solid with about 85% yield and >about 99% purity.

In a third embodiment of the first aspect, the compound

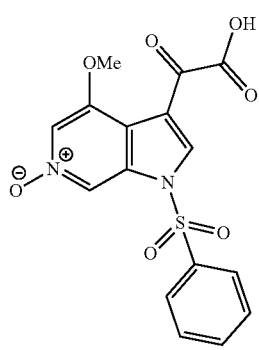 [SMILES: COc1c[n+]([O-])cc2c1c(C(=O)C(=O)O)cn2S(=O)(=O)c1ccccc1]

obtained in step (a) is a crystalline solid which is not isolated.

In a fourth embodiment of the first aspect, the bromination is carried out in the presence of a bromide source such as tetraoctyl ammonium bromide, an activating agent such as methanesulfonic anhydride, and a boroxine compound such as triphenylboroxine.

In a fifth embodiment of the first aspect, the deprotection reaction is carried out using toluene in conjunction with isopropyl alcohol (IPA).

In a sixth embodiment of the first aspect, the compound of formula I

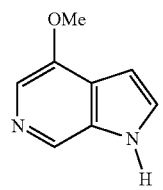 [SMILES: COc1cncc2[nH]ccc12]

is obtained with a yield ranging from about 67.1% to 70.3%, and purity ranging from about 98.5 to 99.7%.

In a second aspect, the present invention provides a process for preparing a compound of formula II

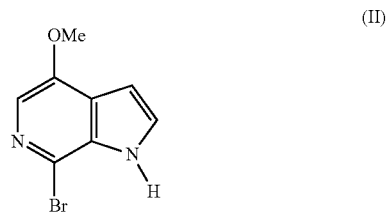 [SMILES: COc1cnc(Br)c2[nH]ccc12]

(II)

said process comprising the steps of:
(a) performing an oxidation reaction on the compound

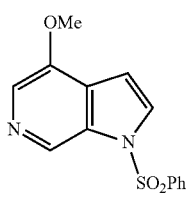

using H$_2$O$_2$, phthalic anhydride, and a solvent to yield the compound

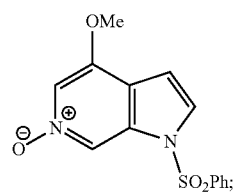

and
(b) performing a bromination reaction on the compound obtained in step (a) using one or more boroxine compounds, along with a bromide source and an activating agent to obtain the compound

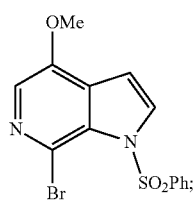

and (c) performing a deprotection reaction on the compound obtained in step (b) using either pure toluene or toluene in combination with a solvent, followed by crystallization, to prepare the compound of formula II or its salts thereof.

In a third aspect, the present invention provides a method of making a compound of formula III

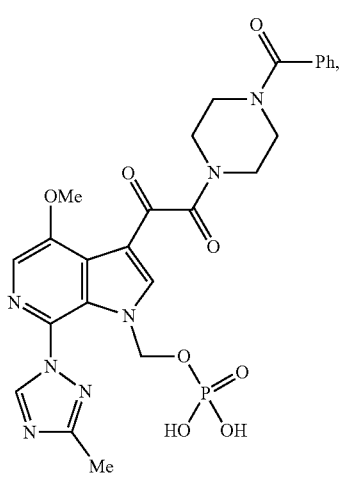

(III)

said process comprising the steps of:
(a) performing an oxidation reaction on the compound

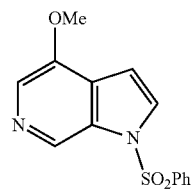

using H$_2$O$_2$, phthalic anhydride and dichloromethane to yield the compound

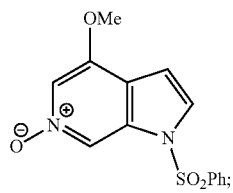

and
(b) performing a bromination reaction on the compound obtained in step (a) using one or more boroxine compounds, along with a bromide source and an activating agent, to obtain the compound

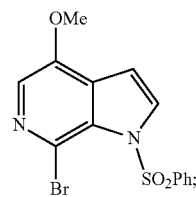

(c) performing a deprotection reaction on the compound obtained in step (b) using either pure toluene or toluene in combination with a solvent, followed by crystallization, to obtain the compound

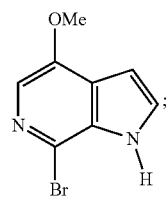

(d) reacting the compound obtained in step (c) to obtain the compound

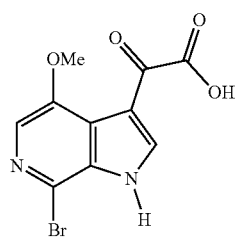 [SMILES: COc1cnc(Br)c2[nH]cc(C(=O)C(=O)O)c12]

followed by an activation reaction and coupling with compound

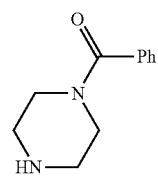

to produce compound

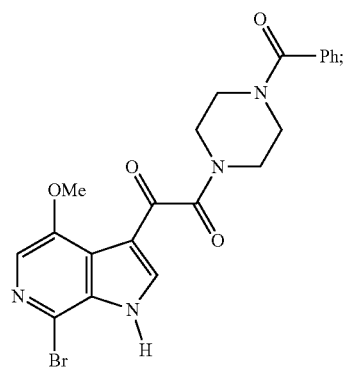 [SMILES: COc1cnc(Br)c2[nH]cc(C(=O)C(=O)N3CCN(C(=O)c4ccccc4)CC3)c12]

and (e) adding the triazolyl compound

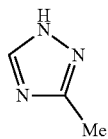

in the presence of Cu ion and a ligand to obtain compound

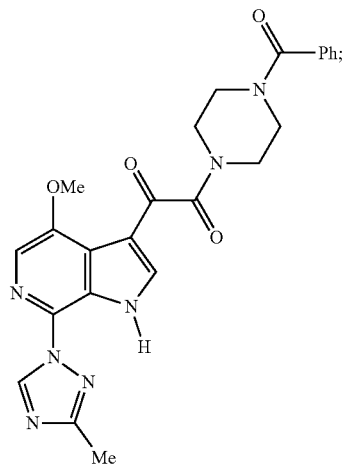 [SMILES: COc1cnc(-n2cnc(C)n2)c2[nH]cc(C(=O)C(=O)N3CCN(C(=O)c4ccccc4)CC3)c12]

wherein said ligand is selected from the group of 1,2-diaminocyclohexane, trans-1,2-diaminocyclohexane, cis-/trans-diaminocyclohexane, cis-N,N'-dimethyl-1,2-diaminocyclohexane, trans-N,N'-dimethyl-1,2-diaminocyclohexane, cis-/trans-N,N'-dimethyl-1,2-diaminocyclohexane, 1,2-diaminoethane, N,N'-dimethyl-1,2-diaminoethane, 1,10-phenanthroline, 4,7-diphenyl-1,10-phenantroline, 5-methyl-1,10-phenanthroline, 5-chloro-1,10-phenantroline, and 5-nitro-1,10-phenanthroline; and (f) reacting the compound obtained in step (e) with (t-BuO)$_2$POOCH$_2$Cl to produce the compound

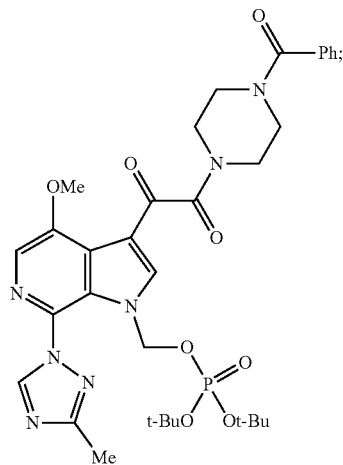 [SMILES: COc1cnc(-n2cnc(C)n2)c2c1c(C(=O)C(=O)N1CCN(C(=O)c3ccccc3)CC1)cn2COP(=O)(OC(C)(C)C)OC(C)(C)C]

and reacting compound obtained in step (f) with an acid, such as acetic acid, to yield the compound of formula III above.

EXAMPLES

The present invention will now be described in connection with certain embodiments which are not intended to limit its scope. On the contrary, the present invention covers all alternatives, modifications, and equivalents as can be included within the scope of the claims. Thus, the following examples, which include specific embodiments, will illustrate one practice of the present invention, it being understood that the examples are for the purposes of illustration of certain embodiments and are presented to provide what is believed to be the most useful and readily understood description of its procedures and conceptual aspects.

The compounds of the present invention may be prepared using the reactions and techniques described in this section, as well as, other synthetic methods which may be available to those of ordinary skill in the art. The reactions are performed in solvents appropriate to the reagents and materials employed and suitable for the transformation being affected. Also, in the description of the synthetic methods described below, it is to be understood that all proposed reaction conditions, including choice of solvents, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents which are compatible with the reaction conditions will be readily apparent to one skilled in the art and alternate methods must then be used.

In a preferred embodiment of the invention, the synthesis of the halogenated azaindole compounds can be set forth in the following non-limiting schematic representation—Scheme I.

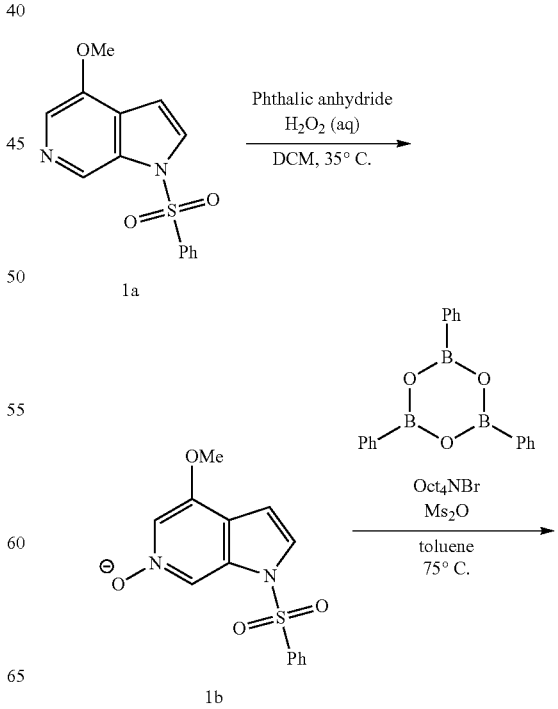

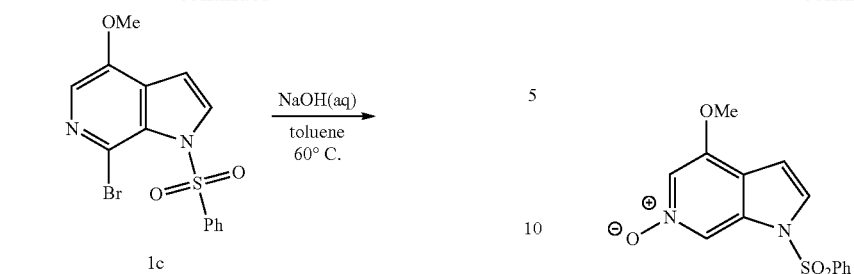
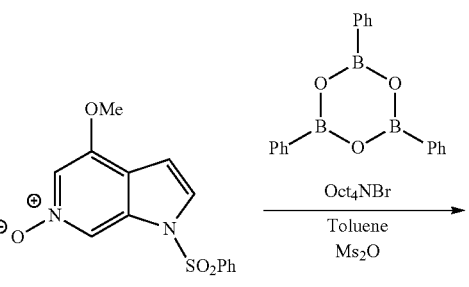
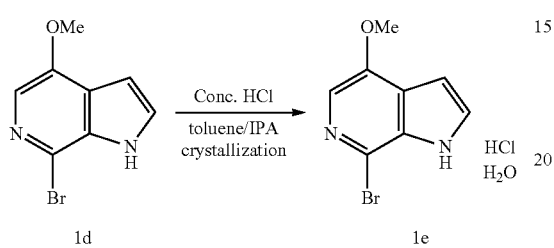
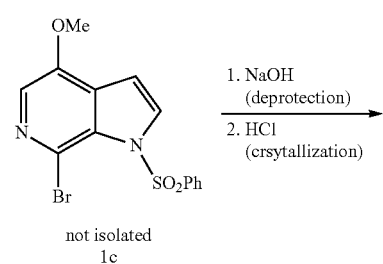

All reagents were used as received without further purification. Reaction progress and final product purity was monitored using HPLC conditions, Table 1, using an Ascentis Express C18, 2.7 μm 4.6×150 mm column at 25° C. Mobile Phase A: 0.01M NH₄OAc in H₂O:MeOH (80:20), Mobile phase B: 0.01 NH₄OAc in H₂O:MeCN:MeOH (5:75:20), 1.0 mL/min. Gradient:

TABLE 1

| | HPLC Conditions | | |
|---|---|---|---|
| Time (minutes) | Mobile Phase Composition % A | % B | Gradient Profile |
| 0.0 | 100.0 | 0.0 | Initial |
| 5.0 | 70.0 | 30.0 | Linear |
| 20.0 | 55.0 | 45.0 | Linear |
| 25.0 | 0.0 | 100.0 | Linear |
| 30.0 | 0.0 | 100.0 | Hold |

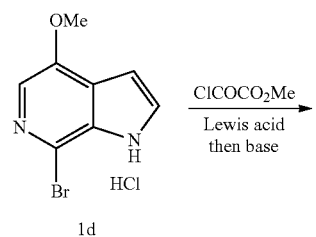
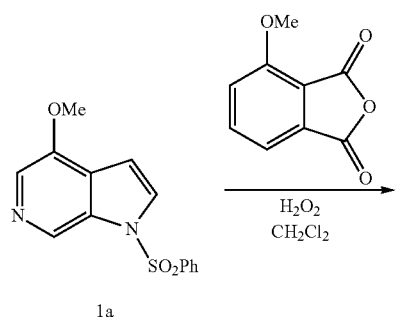
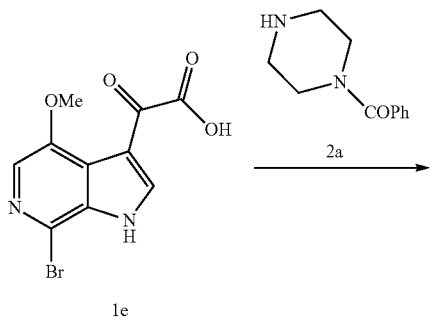
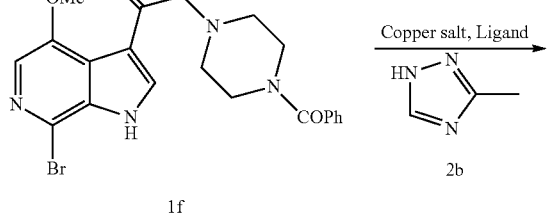

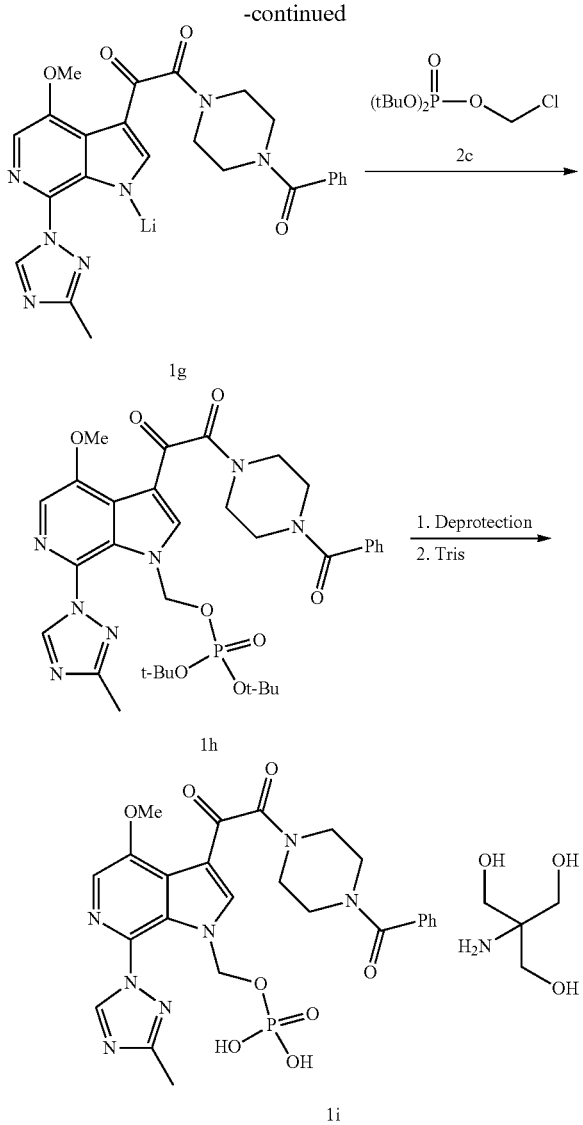

7-Bromo-4-methoxy-1H-pyrrolo[2,3-c]pyridine hydrochloride monohydrate (1d)

CH$_2$C$_2$ (2660 L), Compound 1a (190 kg, 1.0 equiv) and phthalic anhydride (127.3 kg, 1.3 equiv) were charged to an 8000 L glass lined vessel, and the resulting mixture was heated to 35° C. A 30% w/w aqueous solution of hydrogen peroxide (76.8 kg, 1.2 equiv) was added via pump over 2 hours. The resulting suspension was stirred at 35-37° C. for an additional 2 hours, then sampled and analyzed by HPLC to determine the reaction progress. Once the oxidation reaction was deemed complete, the mixture was cooled to 10° C. The reaction was quenched by controlled addition of a solution of sodium sulfite (85.5 kg, 1 equiv) in water (1330 kg) such that the internal temperature remained below 20° C. The resulting biphasic mixture was stirred vigorously at 20° C. for 2 hours to ensure complete reduction of any residual oxidant. A solution of K$_3$PO$_4$ (353 kg) in water (1330 kg) was then added to the quenched reaction mixture and the biphasic mixture stirred at 20° C. for 2 hours. The top aqueous phase was discarded and the lower product-rich organic phase was washed with water (1330 kg). The bottom product-rich organic phase was transferred to a clean 8000 L reactor.

Toluene (1900 L) was added, and the batch was concentrated at ≤0.075 MPa while maintaining the jacket temperature below 40° C. to a final volume of 3000 L. Toluene was added (1900 L) two more times with similar concentrations to volume batch volume of 3000 L in order to meet the specifications for KF (<200 ppm) and DCM (dichloromethane) (<1 wt %). The batch was cooled to 20° C. and toluene (1900 L) was added. Tetraoctylammonium bromide (450.4 kg, 1.25 equiv) and triphenylboroxine (267 kg, 1.3 equiv) were added, and the mixture was agitated for 1 h. Methanesulfonic anhydride (275.5 kg, 2.4 equiv) and toluene (413 kg) were then added and the mixture agitated for 30 min. The slurry was heated to 75° C. for 10 h, then sampled and analyzed. During this time the reaction mixture transformed from a thick slurry to a homogenous solution. After completion of the bromination reaction, the batch was concentrated at ≤0.075 MPa while maintaining the jacket temperature below 40° C. to a final volume of 3000 L. The resulting slurry was cooled to 25° C. and acetonitrile (1200 kg) was added and agitated for 2 h. The slurry was filtered and the solids were rinsed with acetonitrile (450 kg). The solids were triphenylboroxine, and can be dried (50° C. under vacuum) and re-used in subsequent bromination reactions. Expected recovery is 60-70% of the input quantity of the triphenylboroxine. To the product-rich filtrate a solution of potassium phosphate tribasic (560 kg, 4 equiv) in water (1678 kg) was added to the reactor at such a rate that the internal temperature was maintained below 35° C. The resulting biphasic mixture was then heated to 40° C. for 2 hours. The batch was cooled to 20° C., the phases were allowed to split and were separated, and the aqueous layer was discarded. To the resulting mixture was added sodium hydroxide (106.4 kg, 4.0 equiv) in water (532 kg), and the mixture was then heated to 60° C. for 4 hours. After reaction completion the batch was cooled to 20° C., and water (950 kg) was added to dissolve solids. The biphasic mixture was polish filtered (1 μm) and then the phases were allowed to split and were separated. The top phase (product-rich) was sequentially washed with: a solution of NaOH (106.4 g, 4 equiv) in water (532 kg), a solution of KH$_2$PO$_4$ (105.9 kg) in water (950 kg), and water (950 kg).

The organic stream was transferred to an 8000 L glass lined vessel and toluene (950 L) was added. The mixture was then concentrated (T≤50° C., 40-90 mbar) to a final volume of 1300 L, at which point the water content of the toluene solution was <1.0 wt. Isopropanol (450 kg) was added and the batch was heated to 40° C. Aqueous HCl (162.5 kg, 35 w/w %, 2.5 equiv) was then added over 3 hours with high agitation. The resulting suspension was cooled to 20° C. over 1 hour and then stirred for 2 hours. The product was collected by centrifugation, washed with a mixture of toluene (400 L) and isopropanol (171 L), a mixture of toluene (752 L) and isopropanol (293 L), and toluene (570 L), and dried at 50° C. at <0.1 MPa to afford the brominated azaindole 1d as an off-white solid, 129.5 kg (99.64 AP, 99.79 wt %, 69.7% corrected yield).

Thus, the halogenated azaindole compounds and the reactions described above can be used in the production of the piperazine prodrug compound as shown further along in the scheme above. Also, in the scheme above, particularly 1e may be converted to 1i using the schemes described in PCT application number PCT/US2013/024880 filed Feb. 6, 2013, entitled "Methods for the Preparation of HIV Attachment Inhibitor Piperazine Prodrug Compound", and incorporated herein in its entirety.

A Friedel-Crafts acylation followed by hydrolysis and amidation produced intermediate 1f. The triazole substituent was then incorporated via a copper-catalyzed Ullmann-Goldberg-Buchwald cross-coupling reaction of 1f and 2b leading to the formation of 1g. Attachment of the phosphate pro-drug by alkylation with 2c followed by hydrolysis and crystallization affords the drug substance 1i.

The effective preparation of the brominated intermediate 1d is an important step for the effective synthesis of compound 1i. The bromination process uses readily available and stable reagents such as triphenylboroxine, Oct$_4$NBr and Ms$_2$O and has several advantages. It provides high selectivity for the desired brominated azaindole and reduces the number of undesired impurities. This translates into higher yields and increased purity (average of 99 wt %). The ability to recycle and reuse the triphenylboroxine (~60%) reagent results in a reduction of the cost of the overall process, and increases the sustainability of the manufacturing process. Initial cost estimations have shown that this process can be ~20-35% less expensive than other preparations of compound 1e.

It will be evident to one skilled in the art that the present invention is not limited to the foregoing disclosure and that it can be embodied in other specific forms without departing from the essential attributes thereof. It is therefore desired that the instant disclosure be considered in all respects as illustrative and not restrictive, reference being made to the appended claims, rather than to the foregoing disclosure, and all changes which come within the meaning and range of equivalency of the claims are therefore intended to be embraced therein.

What is claimed is:

1. A process for preparing a compound of formula III

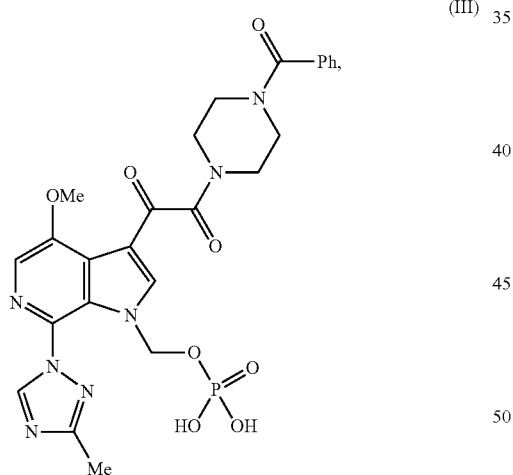

said process comprising the steps of:
(a) performing an oxidation reaction on the compound

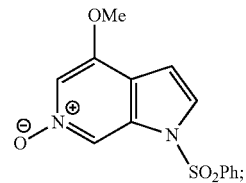

using

H$_2$O$_2$, phthalic anhydride and dichloromethane to yield the compound

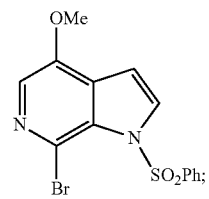

and (b) performing a bromination reaction on the compound obtained in step (a), wherein said bromination is carried out in the presence of a bromide source which is tetraoctyl ammonium bromide, an activating agent which is methanesulfonic anhydride, and a boroxine compound which is triphenylboroxine, to obtain the compound

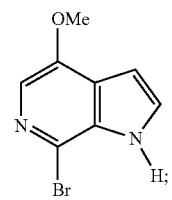

(c) performing a deprotection reaction on the compound obtained in step (b) followed by crystallization, to obtain the compound

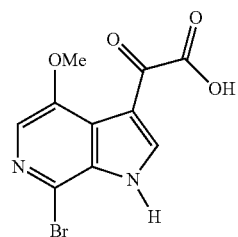 [SMILES: COc1cnc(Br)c2[nH]cc(C(=O)C(=O)O)c12]

(d) reacting the compound obtained in step (c) to obtain the compound

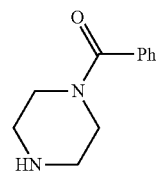 [SMILES: O=C(c1ccccc1)N1CCNCC1]

followed by an activation reaction and coupling with compound

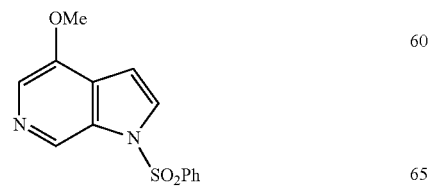

to produce the compound

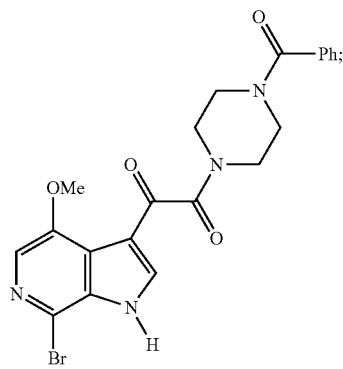 [SMILES: COc1cnc(Br)c2[nH]cc(C(=O)C(=O)N3CCN(C(=O)c4ccccc4)CC3)c12]

and
(e) adding the triazolyl compound

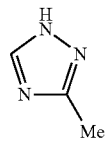

in the presence of Cu ion and a ligand to obtain the compound

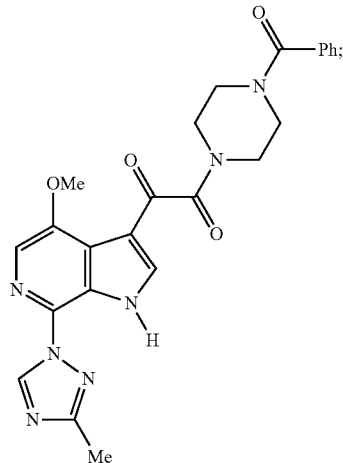 [SMILES: COc1cnc(-n2cnc(C)n2)c2[nH]cc(C(=O)C(=O)N3CCN(C(=O)c4ccccc4)CC3)c12]

wherein said ligand is selected from the group of 1,2-diaminocyclohexane, trans-1,2-diaminocyclohexane, cis-/trans-diaminocyclohexane, i-dimethyl-1,2-diaminocyclohexane, trans-N,N'-dimethyl-1,2-diaminocyclohexane, cis-/trans-N,N'-dimethyl-1,2-diaminocyclohexane, 1,2-diaminoethane, i-dimethyl-1,2-diaminoethane, 1,10-phenanthroline, 4,7-diphenyl-1,10-phenantroline, 5-methyl-1,10-phenanthroline, 5-chloro-1,10-phenantroline, and 5-nitro-1,10-phenanthroline; and (f) reacting the compound obtained in step (e) with $(t\text{-BuO})_2\text{POOCH}_2\text{Cl}$ to produce the compound

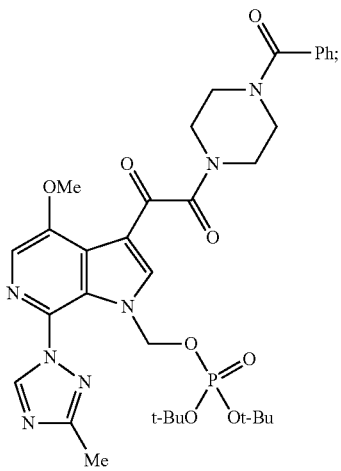 [SMILES: COc1cnc(-n2cnc(C)n2)c2c1c(C(=O)C(=O)N1CCN(C(=O)c3ccccc3)CC1)cn2COP(=O)(OC(C)(C)C)OC(C)(C)C]

and reacting the compound obtained in step (f) with an acid to yield the compound of formula III.

2. The process of claim 1, wherein said acid is acetic acid.

* * * * *